United States Patent [19]

Daviduk et al.

[11] 4,431,856

[45] * Feb. 14, 1984

[54] FLUID ZEOLITE CATALYST CONVERSION OF ALCOHOLS AND OXYGENATED DERIVATIVES TO HYDROCARBONS

[75] Inventors: Nicholas Daviduk, Pennington; James H. Haddad, Princeton Junction, both of N.J.

[73] Assignee: Mobil Oil Corporation, New York, N.Y.

[*] Notice: The portion of the term of this patent subsequent to May 4, 1999 has been disclaimed.

[21] Appl. No.: 361,154

[22] Filed: Mar. 23, 1982

Related U.S. Application Data

[63] Continuation-in-part of Ser. No. 192,151, Sep. 29, 1980, Pat. No. 4,328,384, which is a continuation-in-part of Ser. No. 89,706, Oct. 30, 1979, Pat. No. 4,238,631.

[51] Int. Cl.³ .............................................. C07C 1/20
[52] U.S. Cl. ...................................... 585/469; 585/639; 585/733
[58] Field of Search ...................... 585/469, 639, 733

[56] References Cited

U.S. PATENT DOCUMENTS

| | | | |
|---|---|---|---|
| 2,422,793 | 6/1947 | McAfee | 196/52 |
| 2,463,434 | 3/1949 | Shankland | 196/52 |
| 2,611,685 | 9/1952 | Yoder | 23/288 |
| 2,617,708 | 11/1952 | Peery | 23/1 |
| 2,618,535 | 11/1952 | Trainer et al. | 23/288 |
| 2,833,699 | 5/1958 | Dicks | 196/52 |
| 2,902,432 | 9/1959 | Codet et al. | 208/113 |
| 3,394,076 | 7/1968 | Bunn, Jr. et al. | 208/164 |
| 3,998,898 | 12/1976 | Chang et al. | 260/668 |

FOREIGN PATENT DOCUMENTS

535869 1/1957 Canada.

Primary Examiner—Curtis R. Davis
Attorney, Agent, or Firm—Alexander J. McKillop; Michael G. Gilman; Stanislaus Aksman

[57] ABSTRACT

Alcohols and related oxygenates are converted in a riser reactor and dense fluid catalyst bed comprising ZSM-5 type catalyst circulated through a plurality of satellite stripping-cooling zones for temperature control. Catalyst utilized comprises from 5 to 30 weight percent coke for activity and selectivity control promoting the formation of olefins and aromatics at temperatures below about 427° C. (800° F.).

21 Claims, 1 Drawing Figure

FLUID ZEOLITE CATALYST CONVERSION OF ALCOHOLS AND OXYGENATED DERIVATIVES TO HYDROCARBONS

CROSS REFERENCE TO RELATED APPLICATIONS

This is a continuation-in-part of the copending application of N. Daviduk and J. H. Haddad, Ser. No. 192,151, filed Sept. 29, 1980, now U.S. Pat. No. 4,328,384, issued May 4, 1982, which, in turn, is a continuation-in-part of U.S. application Ser. No. 89,706, filed Oct. 30, 1979, now U.S. Pat. No. 4,238,631, issued Dec. 9, 1980.

BACKGROUND OF THE INVENTION

1. Field of the Invention

This invention relates to an improved method of converting lower alcohols and related oxygenates either to gasoline boiling point range hydrocarbons or to olefin-enriched chemical feedstock.

2. Description of Prior Art

The application of fluidized catalyst techniques, developed particularly in the petroleum industry for effecting chemical reaction embodying the distribution of heat and/or the disposal of undesired heat, has long been accepted as a major processing tool of the industry. For example, fluidized catalyst techniques have been particularly useful for catalytic cracking of oil vapors to produce lower boiling products and regeneration of the catalyst used in such an operation. It has also been proposed to use the fluidized catalyst techniques, primarily for the disposal of generated heat, in the highly exothermic reactions of Fischer-Tropsch synthesis and the known Oxo process and in other such exothermic processes. In the fluidized catalyst operations previously developed, disposal of the reaction heat has been accomplished by many different techniques, for example by transfer of catalyst through cooling sections. Not only are these prior art catalyst techniques used for temperature control by addition and/or removal of heat, but they have also been found useful for maintaining selective conversions and extending the active life of the catalyst used in the process.

The conversion of lower alcohols, such as methanol, to intermediate ether products, e.g., dimethyl ether, followed by conversion of the ether product to one or a combination of products comprising olefins, paraffins, and/or aromatics has been the subject of several patents. Such patents include U.S. Pat. Nos. 3,480,408; 3,928,483; 3,931,349; 3,969,426; 3,998,898; 3,988,899; 4,013,732; 4,035,430; 4,044,061; 4,046,825; 4,052,479; 4,058,576; 4,062,905; 4,071,573; 4,076,761; 4,118,431 and 4,138,440, the entire contents of all of which are incorporated herein by reference.

In prior art processes conversion was usually carried out completely to maximize the production of $C_5^+$ gasoline boiling point range hydrocarbons.

SUMMARY OF THE INVENTION

One embodiment of the present invention is concerned with effecting the conversion of lower alcohols, such as methanol, ethanol and propanol, related oxygenates, such as ether derivatives thereof, and/or mixtures of alcohols and oxygenates in a fluidized mass of catalytic particulate material comprising a selected class of crystalline zeolite, to hydrocarbons comprising primarily gasoline boiling range hydrocarbons. The class of zeolites used in the present invention has a pore dimension greater than about 5 Angstroms, pore windows of a size provided by 10-membered rings of oxygen atoms, a silica/alumina ratio of at least 12 and a Constraint Index in the range of 1 to 12.

Another embodiment of the present invention relates to a separate method of converting these same lower alcohols, related oxygenates, and/or mixtures of alcohols and oxygenates, in the presence of the same class of crystalline zeolites in a fluidized bed reactor, to a hydrocarbon product enriched in olefins suuitable as petrochemical products or feedstocks.

The present invention is also concerned with an arrangement of apparatus for effecting the catalytic conversion of alcohols, aforementioned oxygenates thereof and/or mixtures of alcohols and oxygenates with a fluid mass of catalyst particles, under temperature restricted conditions, to achieve high yields of a hydrocarbon product comprising either primarily gasoline boiling range hydrocarbons or a hydrocarbon product enriched in olefins.

In both process embodiments, the present invention is concerned with the conversion of methanol, or a mixture of lower alcohols and related oxygenates, such as ethers, aldehydes and ketones, in the presence of a special type of zeolite catalyst maintained in an upflowing fluid condition comprising a dispersed catalyst phase riser contact zone discharging into a more dense upflowing fluid mass of catalyst particles. The feed, initially charged in liquid and/or vaporous condition, may be unpurified or a relatively pure methanol or other lower alcohol, or may comprise an ether derivative thereof as a part of the feed.

In our previous U.S. Pat. No. 4,238,631, we disclosed a method whereby the initial conversion in the riser of the methanol feed to dimethylether intermediate was carried out to at least 70% of theoretical completion prior to passing the reaction mixture to the second relatively dense fluid mass of catalyst particles for final conversion thereof to $C_1$ to $C_{10}$ hydrocarbons. In a previous application Ser. No. 192,151, filed Sept. 29, 1980, now U.S. Pat. No. 4,328,384, we disclosed a method whereby the initial conversion of the methanol-containing feed, that is the conversion carried out in the first relatively dispersed catalyst phase riser contact zone, may be desirably carried out for a time, temperature and pressure suitable to achieve up to 70% conversion of methanol and other oxygenates in the reactant feed, while the subsequent conversion in the dense phase bed is such that the total conversion is at least 90% on a once through basis.

In the present invention, the production of light and heavy olefins is maximized by carrying out the conversion in the first relatively dispersed catalyst phase riser zone at such time, temperature and pressure conditions so as to achieve about 15% to about 40% by weight conversion in the riser zone, and maintaining such conversion conditions in the dense phase bed so that the total conversion (defined as the sum of the conversions in the riser and in the dense phase bed, on a single throughput basis) is 90% by weight or less.

DETAILED DESCRIPTION OF THE INVENTION

The term hydrocarbons comprising primarily gasoline or gasoline boiling range hydrocarbons is used herein to designate a product made in one embodiment of the present invention and comprising about 15% to about 25% by weight, on the basis of the total product hydrocarbon content, of olefin hydrocarbons having two or more carbon atoms ($C_2+$). The remainder of such product comprises primarily gasoline boiling point range hydrocarbons of five to ten carbon atoms, a small amount (5-12% by weight) of liquefied petroleum gas (LPG), and light hydrocarbon gases ($C_1$-$C_4$, predominantly $C_1$-$C_2$).

Conversely, the term hydrocarbon product enriched in olefins is used herein to designate a product made in the alternative embodiment of the invention and comprising about 25% to about 67% by weight, preferably about 25% to about 45% by weight, on the basis of the total product hydrocarbon content, of $C_2+$ olefins. Majority of the olefins in this product have two to five ($C_2$-$C_5$) carbon atoms. The remainder of such product is comprised of gasoline boiling point range hydrocarbons, a small amount of LPG, and light hydrocarbon gases ($C_1$-$C_4$, predominantly $C_1$-$C_2$).

In a particular operation of the apparatus of the invention, a liquefied or vaporized alcohol feed, or a mixture of liquified and vaporized feed, with or without related oxygenates, is mixed with the zeolite catalyst charged to the bottom of the riser contact zone (as more particularly discussed below) to form a suspension for flow upwardly through the riser. If it is desired to maximize the production of gasoline boiling point hydrocarbons, if operating in a vaporized feed mode, it is desirable to restrict the catalyst charged to the dispersed catalyst phase in the riser to a temperature of about 322° C. (612° F.) while employing a catalyst to feed ratio of about 10 to about 1 and, when employing a 20 to 1 ratio, the catalyst temperature is preferably restricted to about 366° C. (690° F.). If operating in a liquid feed mode, it will be found desirable to employ higher temperatures and/or catalyst-to-feed ratios, if the embodiment maximizing the production of gasoline is practiced. The dispersed catalyst phase suspension is passed through a riser contact zone of at least 20 feed in length, and more preferably from 25 feet up to about 70 feet in length, before encountering a distributor grid across the bottom of a larger diameter more dense fluid mass of catalyst thereabove. In this arrangement, the reactant residence time in the riser will vary within the process restrictions herein identified.

It is contemplated providing in the riser contact zone a residence time of 1 to 10 seconds. In the more dense phase of catalyst thereabove, a reactant product residence time in contact with catalyst is within the range of 3 to 80 seconds.

The exothermic operation contemplated within the above operating constraints is predicated upon a catalyst concentration within the riser contact zone within the range of 1 to 10 pounds per cubic foot and in the range of 10 to about 40 pounds per cubic foot in the more dense catalyst bed phase above the grid. The temperature constraints of the operation are selected to restrict the product outlet of the dense fluid bed of catalyst to below 427° C. (800° F.), and preferably the temperature is not substantially above 407° C. (765° F.). The pressure of the operation is maintained low, generally not above about 4 atmospheres. It is preferred that the reactor pressure at the bottom of the dense bed be restricted to within the range of 0.3 to 2.5 atmospheres.

These conditions allow the conversion of the feed with minimum contact of the feed with the final desired products. The reaction path for methanol conversion to hydrocarbons shows that very high space velocities, within the range of about 50 to 200 such as occur in a dilute catalyst phase, cause methanol to be converted to dimethyl ether and water. This conversion is up to about 70% completed, if gasoline boiling point hydrocarbons are produced, before any significant quantities of aromatics are formed.

The initial step of methanol conversion to dimethyl ether and water is important since methanol and aromatics readily combine to form tetramethylbenzene (durene) in greater than desirable quantities. Undesirably high quantities of durene would be produced if methanol were injected directly into a fluid mass of catalyst characterized by good backmixing. The desired hydrocarbon products of this embodiment, i.e., gasoline-grade hydrocarbons preferably comprising hydrocarbons of 5 to 10 carbon atoms ($C_5+$ to $C_{10}-$), are obtained usually at the low space velocities in the range of 0.5 to 3.0. This is the space velocity range within which the upper or dense catalyst phase bed is operated in this embodiment. Secondary products of this embodiment comprise light olefins, paraffins, isoparafins and naphthenes.

In this embodiment, the apparatus of this invention causes a very large portion of the methanol feed to be converted into dimethylether and olefins in a dilute catalyst phase riser reactor prior to contact with significant quantities of higher boiling materials, including aromatics, and the remaining conversion thereof to desired hydrocarbons of gasoline-boiling range in the upper more dense catalyst phase of the reactor arrangement. The disclosed method of operation prevents or substantially reduces the occurrence of reactions proceeding to the formation of substantial amounts of paraffins and aromatics and minimizes backmixing of the reactant feed with aromatic products.

In the alternative embodiment of this invention, the operating conditions are selected to maximize the formation of olefin enriched product, usually comprising olefins, paraffins, isoparaffins and naphthenes, and minimize the formation of the gasoline-boiling point range hydrocarbons having five or more carbon atoms ($C_5+$). The operating conditions for this embodiment include the overall operating pressure in the reactor bed (in both the riser and the dense bed) of about 5 to 100 psig, preferably less than about 35 psig; the overall reactor weight hourly space velocity (WHSV) of about 0.5 to about 15, preferably about 1.0 to about 10 WHSV, and most preferably about 1.0 to about 5.0 WHSV; and the rate of catalyst circulation in the riser of about 10 to about 25 pounds of catalyst per pound of total reactor feed. In this embodiment, conversion of the feed in the riser portion of the reactor is maintained at about 15% to about 40% by weight, on a total feed basis (i.e., including recycle) and overall conversion (i.e., total sum of conversions in the riser and in the dense bed) is up to 90% by weight, preferably up to 75% by weight. The term conversion as used herein and in the appended claims for both embodiments, is used to designate conversion of the feed (including alcohols, e.g., methanol, ethanol, propanol, and other oxygenates, e.g., dimethyl ether, aldehydes and ketones) introduced into the riser on a once through basis, i.e., without considering additional conversion of the uncoverted portion of the feed recycled into the reactor. In this embodiment, temperature of the reaction is maintained at a lower level than in the embodiment maximizing the production of gasoline boiling point range hydrocarbons of more than five carbon atoms. The temperature in the dilute phase of the riser is about 530° F. (277° C.) to about 700° F. (371° C.), and in the dense bed phase about 600° F. (316° C.) to about 800° F. (472° C.), preferably about 600° F. to about 700° F. (371° C.). In this embodiment, regeneration of the catalyst is intentionally maintained at below maximum efficiency to provide less active catalyst than in the embodiment maximizing the formation of gasoline boiling point-range hydrocarbons. Accordingly, the conversion of the feed is substantially terminated at the point wherein the formation of olefins is maximized. The catalyst regeneration is carried out to such a degree that the regenerated catalyst contains about 5% to about 30%, preferably about 10% to about 20% by weight of coke.

By maintaining such substantially high coke level on the catalyst, and thereby reducing the catalyst activity, olefins are preferentially produced for a given space velocity under selected temperature conditions. As mentioned above, the high coke level may be maintained by any convenient method, for example, by a limited regeneration of a portion of the catalyst recovered from the reaction zone. The regeneration can be limited, for example, by controlling the amount or concentration of oxygen available to burn the coke on the catalyst or by adjusting the regeneration conditions (such as catalyst residence time in the regenerator) to achieve the desired coke level on the catalyst.

In the embodiment maximizing the production of gasoline boiling point range hydrocarbons, the methanol conversion operation of this invention is one which requires and is designed to obtain substantial restriction of the reactant vapor bubble growth to low orders of magnitude. Thus, the vapor-catalyst hydraulic relationship in the contact zone is restricted by baffles, tubes or a combination thereof, or by any other suitable apparatus means therein, which will restrict the free space and provide a surface area of the baffles equivalent to a hydraulic radius not to exceed about 8 inches and preferably not more than about 1 inch. Bubble dispersing means in the catalyst contact zones, and particularly the dense fluid bed catalyst contact zone, may also be accomplished with some success with Pall type rings of desired relatively large size, vertically displaced baffle means, such as honeycomb sections or portions thereof permitting transverse flow, sections of Blitsch grid, perforated pipe sections, and other known baffling means suitable for the purpose. It is particularly desirable, however, to use elongated open or closed end tubes vertically distributed in the most dense fluid bed and perforated in the walls thereof to provide the surface area above identified and transverse flow of catalyst particles in suspension.

In the embodiment maximizing the production of olefins, baffles or other bubble dispersing means are not usually required in the dense phase reaction zone because it is desirable, to the degree that is possible, to limit the conversion of light olefins to heavier hydrocarbons (e.g., heavier olefins, paraffins and aromatics). Alternatively, baffles or other bubble dispersing means may be provided in the dense phase reaction zone to increase the conversion of methanol at higher feed rates of methanol per pound of catalyst by constraining bubble growth to maximize contact of catalyst particles with the reactants.

The dispersed catalyst phase riser reactor of this invention may be a single large diameter riser reactor tube. Alternatively, a plurality of smaller diameter riser tubes, such as 3 or 4 or more separate riser tubes bundled adjacent to one another or separated from one another, as desired, may be employed in place of a single riser tube. Charging catalyst and alcohol reactant in either vapor or liquid form to the bottom of each riser reactor tube to form a suitable suspension may be accomplished by conventional techniques known in the prior art to provide an upflowing suspension of the desired particle concentration.

The crystalline zeolites utilized herein are members of a special class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. These zeolites, used as catalysts, generally have low coke-forming activity and therefore are conducive to long times on stream between regenerations by burning carbonaceous deposits with oxygen-containing gas, such as air.

An important characteristic of the crystal structure of this class of zeolites is that it provides a selective constrained access to and egress from the intracrystalline free space by virtue of having an effective pore size intermediate between the small pore Linde A and the large pore Linde X, i.e., the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred in some instances to use zeolites having substantially higher silica/alumina ratios, e.g. at least 30. Also to be included within this definition are substantially pure silica analogs of the useful zeolites described herein, that is, those zeolites having no measurable amount of aluminum (silica to alumina mole ratio of infinity) but which otherwise embody the characteristics disclosed herein.

The special class of zeolites, after activation, acquires an intracrystalline sorption capacity for normal hexane which is greater than that for water, i.e., they exhibit "hydrophobic" properties. This hydrophobic character can be used to advantage in some applications.

The special class of zeolites useful herein has an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a hydrogen to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

Constraint Index =

$$\frac{\log_{10} (\text{fraction of hexane remaining})}{\log_{10} (\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|  | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables, such as crystal size of the zeolite, the presence of occluded contaminants, etc., may affect the Constraint Index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined particular class of highly siliceous zeolites are those zeolites which, when tested under two or more sets of conditions within the above-specified ranges of temperature and conversion, produce a value of the Constraint Index slightly less than 1, e.g., 0.9, or somewhat greater than 12, e.g., 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant zeolite class definition whether or not the same identical zeolite, when tested under other of the defined conditions, may give a Constraint Index value outside of the range of 1 to 12.

The particular class of zeolites defined herein is exemplified by ZSM-5, ZSM-11, ZSM-12, ZSM-23, ZSM-35, ZSM-38, ZSM-48 and other similar materials.

ZSM-5 is described in greater detail in U.S. Pat. No. 3,702,886, Re. 29,948, and 3,941,871, the entire contents of all of which are incorporated herein by reference.

ZSM-11 is described in U.S. Pat. No. 3,709,979, the entire content of which is incorporated herein by reference.

ZSM-12 is described in U.S. Pat. No. 3,832,449, the entire content of which is incorporated herein by reference.

ZSM-23 is described in U.S. Pat. No. 4,076,842, the entire content of which is incorporated herein by reference.

ZSM-35 is described in U.S. Pat. No. 4,016,245, the entire content of which is incorporated herein by reference.

ZSM-38 is described in U.S. Pat. No. 4,046,859, the entire content of which is incorporated herein by reference.

ZSM-48 is described in European Patent Application No. 800,300,463, published Sept. 3, 1980 as Publication No. 0,015,132, the entire content of which is incorporated herein by reference.

It is to be understood that by incorporating by reference the foregoing patents to describe examples of specific members of the zeolite class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments, such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38, and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites can maximize the production of gasoline boiling point range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original akali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing the methanol conversion process of the present invention, it is useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in any conversion processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The present invention is concerned with an arrangement of apparatus and the method of using catalyst of selected activity therein for effecting the exothermic conversion of lower alcohols and related oxygenates with a fluid mass of catalyst particles in a manner particularly promoting and selecting the formation of olefinic, paraffinic, naphthenic and aromatic compounds. More particularly, the present invention is concerned with a method and apparatus employed for dispersing the exothermic heat of chemical reaction, generated in the production of the aforementioned hydrocarbons, by contacting a fluidized catalyst, preferably comprising a ZSM-5 crystalline zeolite, with one or more reactants selected from the group consisting of alcohols, ethers, carbonyl compounds, and mixtures thereof.

The term lower alcohols is used herein to designate either purified lower alcohols or unpurified alcohols which have not been treated to remove impurities produced in the manufacturing process. For example, crude methanol, as known in the art, is methanol freshly produced in a methanol plant. Such crude methanol has not been purified and it may contain a number of impurities, e.g., other alcohols, such as ethanol, propanol, butanol; oxygenates, such as ketones, aldehydes; a substantially higher amount of water—up to 30% by weight—than purified alcohol; and some gases, such as $CO$, $CO_2$, $H_2$ and $CH_4$.

Figure 1:
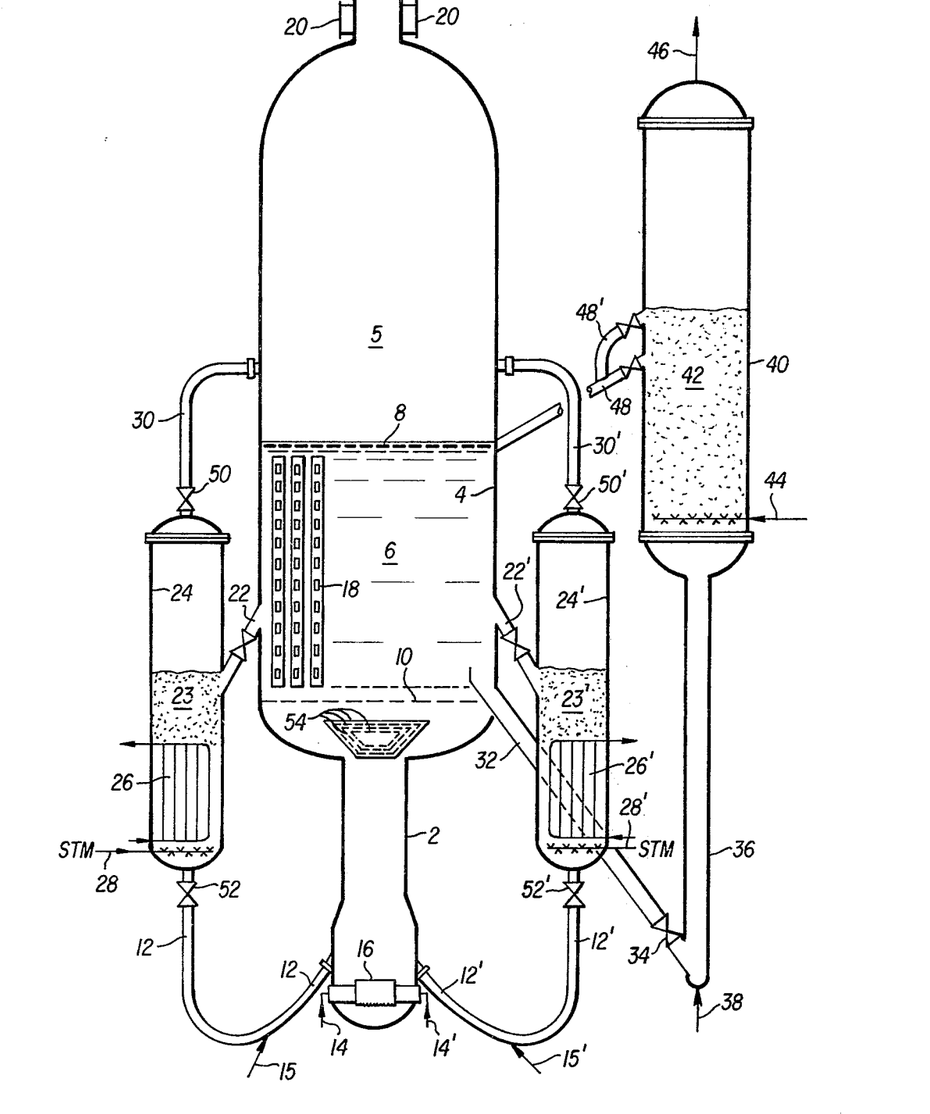
The drawing is a diagrammatic representation, in elevation, of one arrangement of apparatus for effecting the catalytic conversion of lower alcohols, ether derivatives and related oxygenates in a fluid catalyst system to form hydrocarbons, including gasoline boiling range hydrocarbons and LPG products, light and heavy olefins.

Referring now to the drawing by way of example, a reactor arrangement is shown comprising a lower riser section 2 in open communication with the bottom of a larger diameter vessel 4 containing a relatively dense fluid bed of catalyst 6 having an upper interface 8. A distributor grid 10 is positioned across the lower bottom portion of vessel 4 and above the outlet of riser 2. Riser section 2 may comprise more than one separate riser, as mentioned above. There may be a plurality of separate riser conduits, such as two, three or four risers, each separately fed with reactant feed and catalyst. In the specific arrangement of the drawing a fluid suspension of catalyst in methanol vapors is formed in the bottom portion of riser 2. Catalyst is charged to the lower portion of riser 2 by "U" bend transfer conduits 12 and 12'. In a preferred alternative embodiment, "U" bend transfer conduits 12 and 12' may instead comprise inclined outputs containing conventional slide-type catalyst control valves. The feed is charged to the bottom of the riser by inlet means 14 and 14' communicating with an inverted pan 16 open in the bottom thereof. The vaporous feed thus introduced mixes with introduced catalyst to form a suspension, thereafter passed through the riser. Catalyst mass 6 may optionally be filled, as shown in the Figure, with a plurality of vertical elongated tubes 18 provided with openings in the wall thereof to restrict bubble growth within the fluid catalyst bed 6.

In the arrangement of the drawing, a reactant material, such as methanol, or methanol and ether, is charged in liquid, vaporous, or a mixture of liquid and vaporous, condition to the bottom of riser 2 by conduits 14 and 14' at a temperature of about 121° C. (250° F.) to about 260° C. (500° F.) for admixture with cooled and stripped recycled catalyst charged by conduits 12 and 12'. In the embodiment maximizing the production of gasoline range hydrocarbons, a suspension mix temperature in the range of 301° C. (574° F.) to 351° C. (664° F.) is formed with the adjusted recycled catalyst and charged vaporous reactant for passage upwardly through the riser represented by riser 2 in essentially a dispersed catalyst phase condition within the range of 1 to 15, and preferably from 2 to 5, pounds of catalyst per cubic foot. In this embodiment, the upflowing suspension in the riser section is maintained under operating conditions to achieve up to 70% conversion of charged methanol, or other oxygen-containing reactants, in the feed before passing through distributor grid 10 and into the bottom of the more dense fluid mass of catalyst 6 thereabove.

In the embodiment maximizing the formation of olefin-enriched hydrocarbon product, the suspension mix temperature in the riser is about 277° C. (530° F.) to about 371° C. (700° F.), and the ratio of the catalyst to the feed in the riser is maintained at about 3 to about 25 pounds, preferably at about 3 to about 15 pounds of catalyst per pound of total feed. In this embodiment, the upflowing suspension in the riser section is maintained under operating conditions to achieve 15% to 40% by weight conversion in the riser reactor. However, in the downstream dense catalyst fluid bed 6, the conversion is such that the overall conversion is 90% or less, preferably not more than 75% by weight.

Completion of the reactions in the embodiment maximizing the production of gasoline boiling range hydrocarbons is accomplished within the dense fluid catalyst bed 6 so that, desirably, at least 99.5% of methanol in the feed is converted to a hydrocarbon product comprising $C_1$ to gasoline boiling range hydrocarbons ($C_{10}^-$) without exceeding an upper temperature limit of about 399° C. (750° F.) to about 427° C. (800° F.), and preferably not above about 407° C. (765° F.). Cyclone separation equipment (not shown) is provided in the upper portion of vessel 4 to effect recovery of entrained catalyst particles from reaction products. Products of reaction are recovered from the vessel by conduits 20 for separation and recovery in downstream equipment (not shown) for the recovery of gasoline boiling range hydrocarbons.

Catalyst is withdrawn from bed 6 by conduits 22 and 22' for transfer and downflow through catalyst stripping and cooling chambers 24 and 24'. In the embodiment maximizing the production of olefins-enriched hydrocarbon product, the catalyst circulation rate through the stripping and cooling chambers 24 and 24' is about 3 to about 15 pounds per pound of feed. In the embodiment maximizing the production of gasoline boiling point range hydrocarbons, the catalyst circulation rate through these chambers 24 and 24' is about 10 to about 20 pounds per pound of feed. Baffles (not shown) may or may not be employed in the upper portion of chambers 24 and 24' and above indirect heat exchange means 26 and 26' which provide high temperature steam and which are positioned in a lower bottom portion of chambers 24 and 24'. Stripping gas, such as steam and preferably recycle gas obtained from the process, is charged to vessel 24 and 24' by conduits 28 and 28' respectively. The stripping gas is preferably introduced below heat exchange means 26 and 26' for stripping the catalyst cooled to a desired temperature and before withdrawal from the strippers. The stripping gas passes generally upwardly through vessels 24 and 24', countercurrent to downflowing catalyst, for the recovery of displacement of strippable hydrocarbons and particularly aromatics from the catalyst at a controlled temperature suitable for recycle to riser 2. Stripped products and stripping gas are removed by conduits 30 and 30' for passage to the dispersed catalyst phase 5 of vessel 4 and removal after cyclone separation (not shown) with reaction products by conduit 20. The stripped catalyst, essentially free of aromatics, passes downwardly through steam developing indirect heat exchange means 26 and 26', during which time the catalyst temperature is reduced to a level suitable for charging to the base of riser 2, as above discussed, and forming a suspension temperature in riser 2 as defined above. The partially cooled catalyst passes from the bottom of strippers 24 and 24' by conduits 12 and 12' communicating with the lower portion of riser 2 as "U" shaped catalyst transfer conduits.

A portion of the catalyst inventory is withdrawn from a bottom portion of bed 6 into a catalyst withdrawal well, provided in the vessel above grid 10, and thence by conduit 32 provided with flow control valve 34 for catalyst regeneration. Generally, the volume of catalyst withdrawn by conduit 32 will be from about 5% to 10% per hour of the total catalyst in the system. The catalyst withdrawn by conduit 32 is passed to the base of a riser 36 wherein it is mixed with a transport gas or lift gas introduced by conduit 38. The lift gas may be an inert gas or it may be a gas mixture used to effect regeneration of the catalyst by a partial removal of deposited coke. A suspension is thus formed in riser 36 and the suspension is passed upwardly through riser 36 into regeneration zone 40 containing a bed of regenerated catalyst 42. A regeneration gas of desired oxygen concentration may be added to the bottom of riser 36 or it may be introduced to a bottom portion of bed 42 by conduit 44 and provided with a suitable distributing grid within vessel 40. A $CO_2$ rich gaseous product of the partial coke burning regeneration operation is recovered from zone 40 by conduit 46 after passing through cyclonic separation means (not shown) normally housed in the upper portion of vessel 40.

Regeneration of the catalyst is accomplished at a relatively low temperature, generally at about 510° C. (950° F.) or less and preferably at 482° C. (900° F.) or less, and under conditions to achieve only a partial removal of coke or carbonaceous deposits rather than to provide a clean burned catalyst for the reasons stated above. Thus, carrying significant levels of coke on the catalyst is used in this lower alcohol and/or related oxygenates conversion operation as a means for controlling catalyst activity and selectivity characteristics. In view of the temperature restrictions in bed 6 of reactor 4, it is necessary to pass a relatively low temperature catalyst of high residual coke from regenerator 40 to catalyst bed 6 by conduits 48 and 48'. On the other hand, regenerated catalyst may be passed directly to stripper 24 for flow downwardly therethrough together with catalyst passed thereto by conduit 22 and thus returned to the circulating catalyst system.

The reactor system above described may comprise more than the two catalyst stripping-cooling zones 24 and 24' shown. In fact, it is contemplated providing four or more of such catalyst stripping-cooling zone arrangements connected to a riser reaction zone to control a commercial system within the limits herein defined.

For example, when gasoline production is maximized at a LHSV of 1.0 and 12% coke by weight on the catalyst, approximately 23% by weight, on the basis of total hydrocarbon product, of $C_2$ and $C_5$ olefins are produced. Lowering the coke level increases catalyst activity and, at the same space velocity, a lower proportion of $C_2$ to $C_5$ olefins would be product, that is, more olefins would be converted to gasoline boiling range aromatics and paraffins.

In the embodiment maximizing the olefin production a higher proportion of feed remains unconverted than in the embodiment maximizing gasoline production. Accordingly, in this embodiment, it is preferred to recycle unconverted methanol, dimethylether and related oxygenates into the riser. Any convenient means (not shown in the Figure), known to those skilled in the art, may be used to recover the recycle from the product stream of the reaction from the fractionation/separation equipment downstream of the reactor.

In the apparatus arrangement of this invention, the pressure in stripper-cooling chambers, and thus the upper level of catalyst retained therein, is controlled by gaseous stripping material withdrawal conduits 30 and 30' which in turn are provided with pressure contact valves 50 and 50'. Thus, the pressure at the bottom of the stripping-cooling chambers is equivalent to the pressure maintained in the dispersed catalyst phase of reactor chamber 4 plus the head of pressure developed by the dense bed of catalyst in vessel 4 through withdrawal conduits 22 or 22' and the dense beds of catalyst 23 and 23' extending downwardly through vessels 24 and 24'. Valves 52 and 52' are used to shut off the flow of catalyst from the bottom of vessels 24 and 24'. Some additional head of pressure is developed in conduits 12 and 12' to at least the bottom of the "U" bend of the catalyst transfer conduit.

The rate of flow of catalyst from the bottom of the "U" bend upwardly therein into the riser reactor 2 for admixture with reactant is controlled by charging gaseous material into the upflowing catalyst by conduits 15 and 15'. The gaseous material charged by conduits 15 and 15' may be inert to the reactions desired or it may be one or more of the hydrocarbon gaseous products of the reaction. Alternatively, the gaseous material thus charged may comprise methanol-containing feed otherwise charged by conduits 14 and 14' to the riser.

In the embodiment wherein gasoline production is maximized, it is also contemplated to admix the feed with some hydrocarbon gaseous products of the reaction. It is particularly advantageous to use recycled ethylene, produced in the reaction and separated in the downstream separation equipment, as the gaseous material admixed with the feed in the conduits 14 and 14' and, optionally, in the conduits 15 and 15'.

It will be recognized by those skilled in the art that, as mentioned above, instead of employing "U" bend catalyst transfer conduits, one may use straight sloping standpipes communicating with the bottom of riser 2. In this arrangement, catalyst flow control valves will be located adjacent the bottom of the standpipe. In this embodiment, the methanol reactant will be charged to the bottom of the riser. This sloping standpipe riser arrangement with feed charged to the bottom of the riser will be generally similar to that shown for the catalyst regeneration arrangement employing standpipe 32, valve 34, riser 36 and gaseous material inlet 38. Of course, there would be a sloping standpipe from each stripping-cooling vessel communicating with the bottom section of the riser reactor.

The apparatus of the invention contemplates relatively high catalyst circulation rates through the stripping-cooling zones as well as through a plurality of cyclone separators in the upper dispersed catalyst phase of reactor vessel 4. Although not specifically shown, it is contemplated employing from 6 to 8 combinations of 3-stage cyclones to achieve separation of catalyst particles from reaction products. Separated catalyst will be returned to the lower bottom portion of bed 6, but above grid 10, by cyclone diplegs suitable for the purpose.

To facilitate distribution of the suspension across the bottom of grid 10 following traverse of riser section 2, a plurality of diverging conical shaped baffles 54, coaxially aligned with the riser and positioned within one another, are provided above the riser outlet in the dish shaped bottom section of vessel 4. The distributed suspension passes through grid 10 and into the bed of catalyst for flow upwardly therethrough about the gas bubble restricting baffles 18 discussed above. The distribution grid 10 is designed to produce bubbles with a diameter of about 2 to about 10 inches, and preferably between about 2 and about 4 inches.

Having thus generally described the apparatus and its method of operation for upgrading feeds comprising lower alcohols and derivatives thereof, and described specific embodiments in support of the disclosure, it is to be understood that no undue restrictions are to be imposed by reasons thereof, except as defined by the following claims.

We claim:

1. A method for converting reactants consisting of lower alcohols, ethers, aldehydes or ketones derivatives thereof and/or any mixtures thereof to hydrocarbon products enriched in olefins which comprises:

passing a suspension of a reactant material and fluid catalyst particles comprising a crystalline zeolite material characterized by a silica to alumina mole ratio of at least 12 and a Constraint Index of within the approximate range of 1–12 upwardly through a relatively dispersed catalyst phase riser contact zone for a time, temperature and pressure suitable to achieve 15% to 40% conversion by weight of the feed;

passing the suspension comprising products of reaction upwardly through a relatively dense fluid mass of catalyst particles for a residence time and temperature sufficient to achieve a total conversion by weight of the feed up to 90% and produce simultaneously hydrocarbon products enriched in olefinic materials;

passing the catalyst withdrawn from said relatively dense fluid mass of catalyst particles downwardly through a plurality of separate catalyst stripping-cooling zones of desired temperature restriction and thence to the riser reactor for admixture with charged vaporous reactant;

passing stripped products from the stripping-cooling zone into admixture with product mixture above said more dense fluid mass of catalyst and withdrawing reaction products separated from said catalyst from an upper portion of said reaction zone.

2. A method of claim 1 wherein the temperature of said dispersed catalyst phase riser contact zone is about 530° F. to about 700° F.

3. A method of claim 2 wherein the temperature of said relatively dense catalyst phase is about 600° F. to about 800° F.

4. A method of claim 3 wherein the residence time and temperature in said relatively dense fluid mass of catalyst particles is such that the total conversion by weight of the feed is about 75% or less.

5. A method of claim 4 wherein the catalyst to reactant weight ratio of the initially formed suspension in the riser is about 3:1 to about 20:1.

6. A method of claim 5 wherein the temperature of said relatively dense catalyst phase is about 600° F. to about 700° F.

7. A method of claim 6 wherein a portion of the circulated catalyst is withdrawn, subjected to a partial regeneration, and thereafter returned to the circulated catalyst inventory, and the partially regenerated catalyst charged to the riser contact zone contains from about 5 to about 30 weight percent coke on the catalyst.

8. A method of claim 7 wherein catalyst circulation through the riser contact zone, dense fluid mass of catalyst thereabove and the stripper-cooling zone is in response to the reactant feed rate and the catalyst pressure at the base of a catalyst transfer zone in communication with said riser contact zone.

9. A method of claim 8 wherein said partial regeneration is conducted at a temperature of about 900° F. or less.

10. A method of claim 1, 2, 3, 4, 5, 6, 7, 8 or 9 wherein said zeolite is chosen from the group consisting of ZSM-5, ZSM-11, ZSM-12, ZSM-23, ZSM-35, ZSM-38 and ZSM-48.

11. A method of claim 10 wherein said zeolite is ZSM-5.

12. A method of claim 10 wherein said zeolite additionally comprises a binder therefor.

13. A method of claim 11 wherein said reactants comprise methanol.

14. A method of claim 12 wherein said reactants comprise dimethyl ether.

15. A method of claim 12 wherein said reactants comprise a mixture of lower alcohols and ethers.

16. A method of claim 12 wherein said reactants comprise a mixture of lower alcohols and aldehydes.

17. A method of claim 12 wherein said reactants comprise a mixture of lower alcohols and ketones.

18. A method of claim 10, wherein the products of the reaction comprise about 25% to about 67% by weight of $C_2^+$ olefins.

19. A method of claim 18 wherein the products of the reaction comprise about 25% to about 45% by weight of $C_2^+$ olefins.

20. A method of claim 17 wherein at least a portion of the products of the reaction is recycled into said relatively dispersed catalyst phase riser contact zone.

21. A method of claim 9 wherein the partially regenerated catalyst charged to the riser contact zone contains about 10 to about 20 weight percent coke on the catalyst.

* * * * *

UNITED STATES PATENT AND TRADEMARK OFFICE
CERTIFICATE OF CORRECTION

PATENT NO. : 4,431,856
DATED : February 14, 1984
INVENTOR(S) : NICHOLAS DAVIDUK and JAMES H. HADDAD It is certified that error appears in the above—identified patent and that said Letters Patent is hereby corrected as shown below:

Column 5, Line 55   "Blitsch" sould be --Glitsch--.

Column 12, Line 21  "outputs" should be --conduits--.

Signed and Sealed this

Twenty-eighth Day of August 1984

[SEAL]

Attest:

GERALD J. MOSSINGHOFF

Attesting Officer   Commissioner of Patents and Trademarks